US009322791B2

(12) United States Patent
Humphry et al.

(10) Patent No.: US 9,322,791 B2
(45) Date of Patent: Apr. 26, 2016

(54) PHASE RETRIEVAL FROM PTYCHOGRAPHY (71) Applicant: PHASE FOCUS LIMITED, Sheffield (GB)

(72) Inventors: Martin James Humphry, Nottingham (GB); Andrew Maiden, Sheffield (GB)

(73) Assignee: PHASE FOCUS LIMITED, Sheffield (GB)

(*) Notice: Subject to any disclaimer, the term of this patent is extended or adjusted under 35 U.S.C. 154(b) by 0 days.

(21) Appl. No.: 14/424,020

(22) PCT Filed: Aug. 29, 2013

(86) PCT No.: PCT/GB2013/052270
§ 371 (c)(1),
(2) Date: Feb. 25, 2015

(87) PCT Pub. No.: WO2014/033459
PCT Pub. Date: Mar. 6, 2014

(65) Prior Publication Data
US 2015/0300964 A1    Oct. 22, 2015

(30) Foreign Application Priority Data
Aug. 31, 2012 (GB) .................................. 1215558.6

(51) Int. Cl.
G01J 1/42          (2006.01)
G01T 1/00          (2006.01)
(Continued)

(52) U.S. Cl.
CPC .......... *G01N 23/20* (2013.01); *G01N 23/20058* (2013.01); *G06K 9/3241* (2013.01); *H04N 5/32* (2013.01)

(58) Field of Classification Search
CPC .................... G01N 23/20; G01N 23/20058
USPC ................................................ 250/395, 336.1
See application file for complete search history.

(56) References Cited

U.S. PATENT DOCUMENTS

2011/0235862 A1*  9/2011  Roberts .................. G01N 23/20
                                                              382/103
2012/0140986 A1   6/2012  Maiden
2015/0108352 A1*  4/2015  Maiden ................. G06T 11/003
                                                              250/336.1

FOREIGN PATENT DOCUMENTS

EP        1978354 A1    10/2008
WO     2006082557 A2     8/2006
(Continued)

OTHER PUBLICATIONS

Maiden et al., "Superresolution Imaging Via Ptychography", Journal of the Optical Society of America, vol. 28, Apr. 1, 2011, pp. 604-612.
(Continued)

*Primary Examiner* — David Porta
*Assistant Examiner* — Meenakshi Sahu
(74) *Attorney, Agent, or Firm* — Lando & Anastasi, LLP (57) ABSTRACT Embodiments of the present invention provide a method of estimating a magnitude of background radiation for each of a plurality of regions of a target object comprising providing an estimate of background radiation detected by a detector, measuring radiation scattered by the target object at the detector for each of a plurality of positions of the object with respect to the incident radiation, calculating, for each of the positions, an estimate of a wavefront at the detector, and determining, for each position, an estimated wavefront comprising a coherent contribution from radiation scattered by the target object and a background contribution, wherein said background contribution is at least partly incoherent with the radiation scattered by the target object. This method is particularly suitable for performing coherent diffractive imaging using ptychography where contribution from the incoherently scattered background is taken into account.

29 Claims, 7 Drawing Sheets (51) Int. Cl.
*G01N 23/20* (2006.01)
*H04N 5/32* (2006.01)
*G06K 9/32* (2006.01)

(56) References Cited

FOREIGN PATENT DOCUMENTS

| WO | 2008035959 A1 | 3/2008 |
|---|---|---|
| WO | 2010035033 A1 | 4/2010 |

OTHER PUBLICATIONS

Martin et al., "A Method for Correcting the Effect of Specimen Drift on Coherent Diffractive Imaging", Ultramicroscopy, 2010, pp. 359-365.

Thibault et al., "3D Reconstructions Using Ptychography and Laminography", European Synchrotron Radiation Facility Experiment Report, Mar. 8, 2012, pp. 1-2.

* cited by examiner

PHASE RETRIEVAL FROM PTYCHOGRAPHY

CROSS-REFERENCE TO RELATED APPLICATIONS

This application is a U.S. National Stage Application under 35 U.S.C. §371 of PCT Application Serial No. PCT/GB2013/052270 filed on Aug. 29, 2013; which claims priority to GB Application No. 1215558.6 filed Aug. 31, 2012, the entire disclosures of which are hereby incorporated herein by reference in their entireties for all purposes.

BACKGROUND

The present invention relates to methods and apparatus for providing image data from which an image of at least a portion of a target object may be generated. In particular, embodiments of the invention relate to methods and apparatus for improving a quality of image data.

WO 2005/106531, which is incorporated herein by reference for all purposes, discloses a method and apparatus of providing image data for constructing an image of a region of a target object. Incident radiation is provided from a radiation source at the target object. An intensity of radiation scattered by the target object is detected using at least one detector. The image data is provided responsive to the detected radiation. A method for providing such image data via an iterative process using a moveable softly varying probe function such as a transmittance function or illumination function is also disclosed. The methods and techniques disclosed in WO 2005/106531 are referred to as a ptychographical iterative engine (PIE).

PIE provides for the recovery of image data relating to at least an area of a target object from a set of diffraction pattern measurements. Several diffraction patterns are recorded at a measurement plane using one or more detectors, such as a CCD or the like. A probe function, which might be a transmittance function associated with a post-target object aperture or an illumination function, must be known or estimated.

WO 2010/064051, which is incorporated herein by reference for all purposes, discloses an enhanced PIE (ePIE) method wherein it is not necessary to know or estimate the probe function. Instead a process is disclosed in which the probe function is iteratively calculated step by step with a running estimate of the probe function being utilised to determine running estimates of an object function associated with a target object.

Other methods of providing image data based on measurement of scattered radiation are also known. Embodiments of the invention may separately determine a coherent contribution and a background contribution to an estimated wavefront.

As noted above, one or more coherent diffraction patterns are recorded at the detector. However, the radiation recorded by the detector may also contain a background that does not relate to the coherent diffraction pattern. The background component may result from a variety of sources. One source of note is as a result of inelastic scattering with the object.

As incident radiation interacts with the object, a portion of the radiation interacts via inelastic scattering. At least some of the radiation having undergone inelastic scattering undergoes a change in wavelength. The change in wavelength results in the detector recording a "halo" which surrounds features formed by the elastically scattered radiation. This halo is incoherent with the elastically scattered features. Other effects from inelastic scattering may also be observed.

It is an object of embodiments of the invention to at least mitigate one or more of the problems of the prior art.

SUMMARY OF THE INVENTION

According to aspects of the present invention there is provided a method and apparatus as set forth in the appended claims.

According to a further aspect of the present invention, there is provided a method of estimating a magnitude of background radiation for each of a plurality of regions of a target object comprising providing an estimate of background radiation detected by a detector, measuring radiation scattered by the target object at the detector for each of a plurality of positions of the object with respect to the incident radiation, calculating, for each of the positions, an estimate of a wavefront at the detector; and, determining, for each position, a scale factor for scaling the estimate of background radiation to reduce a difference between a combination of the estimate of the background radiation and an estimated wavefront, and the measured radiation.

The estimate of the background radiation may be provided by determining an estimate of a probe function for the background radiation at a plane of the object; and propagating the estimate to the plane of the detector.

Determining the estimate of the probe function may comprise selecting a portion of the estimate of the probe function corresponding to elastically scattered radiation and setting the portion to one or more predetermined values.

Selecting may comprise applying a mask to the estimate of the probe function and setting the portion within the mask to the one or more predetermined values.

The estimate of the background radiation may be provided by propagating an estimate of a probe function at a plane of the object to a plane of the detector; and removing a free space diffraction pattern from the estimate at the plane of the detector.

The scale factor may be applied to the estimate of background radiation to reduce a difference between a sum of the estimate of the background radiation and an estimated wavefront, and the measured radiation.

The scale factor may be determined by a fitting process to determine the scale factor having a minimum difference between a combination of the estimate of the background radiation and an estimated wavefront, and the measured radiation.

The scale factor $\gamma_j$ may be determined to find a minimum value of:

$$|\sqrt{I_j(u)} - \gamma_j S(u) - \psi_j(u)|$$

where $I_j(u)$ is an intensity of radiation measured by the detector for the position j, $S(u)$ is the estimate of background radiation detected by the detector, $\psi_j(u)$ is the estimated wavefront.

The method may comprise storing the scale factor for each of the plurality of positions in a multi-dimensional array.

The estimate of a wavefront at the detector may be determined by a ptychography method.

The estimate of a wavefront at the detector may be determined by multiplying an object function estimate with a probe function estimate to determine an exit wavefront, and propagating the exit wavefront to the plane of the detector.

At least one of the object function and the probe function may be updated based upon the measured radiation and the scaled background radiation to provide an improved estimate of the respective at least one of the object function and the probe function.

According to a further aspect of the present invention, there is provided an apparatus, comprising a memory storing an estimate of background radiation detected by a detector and data indicative of radiation scattered by a target object for each of a plurality of position of the object with respect to the incident radiation a processor arranged to determine an estimate of a wavefront at the detector and, for each position, a scale factor for scaling the estimate of background radiation to reduce a difference between a combination of the estimate of the background radiation and the estimate of the wavefront, and the measured radiation.

The scale factor may be applied to the estimate of background radiation to reduce a difference between a sum of the estimate of the background radiation and an estimated wavefront, and the measured radiation.

The processor may be arranged to perform a fitting process to determine the scale factor resulting in a minimum difference between a combination of the estimate of the background radiation and an estimated wavefront, and the measured radiation.

The scale factor $\gamma_j$ is determined to find a minimum value of:

$$|\sqrt{I_j(u)} - \gamma_j S(u) - \psi_j(u)|$$

where $I_j(u)$ is an intensity of radiation measured by the detector for the position j, S(u) is the estimate of background radiation detected by the detector, $\psi_j(u)$ is the estimated wavefront.

The apparatus may be arranged to store the scale factor for each of the plurality of positions in a multi-dimensional array in the memory.

The apparatus may comprise a detector for measuring an intensity of radiation scattered by the target object.

According to a further aspect of the present invention, there is provided a method of estimating a magnitude of background radiation for each of a plurality of regions of a target object comprising providing an estimate of background radiation detected by a detector; measuring radiation scattered by the target object at the detector for each of a plurality of positions of the object with respect to the incident radiation; calculating, for each of the positions, an estimate of a wavefront at the detector; and determining, for each position, an estimated wavefront by determining a first object function corresponding to a coherent contribution from radiation scattered by the target object and determining a second object function corresponding to a background contribution from incoherently scattered radiation.

The first object function may be determined based on a portion of a portion of an estimated probe function corresponding to elastically scattered radiation. The second object function may be determined based on a portion of an estimated probe function corresponding to a further portion of the probe function.

In embodiments of the invention the coherent contribution and the background contribution may be separately determined.

BRIEF DESCRIPTION OF THE DRAWINGS

Embodiments of the invention will now be described by way of example only, with reference to the accompanying figures, in which.

DETAILED DESCRIPTION OF EMBODIMENTS
OF THE INVENTION

Embodiments of the invention are arranged to produce an incoherent background map of at least a region of an object, wherein the map indicates a contribution of each of a plurality of regions of the object to incoherent background radiation recorded by a detector.

Figure 1:
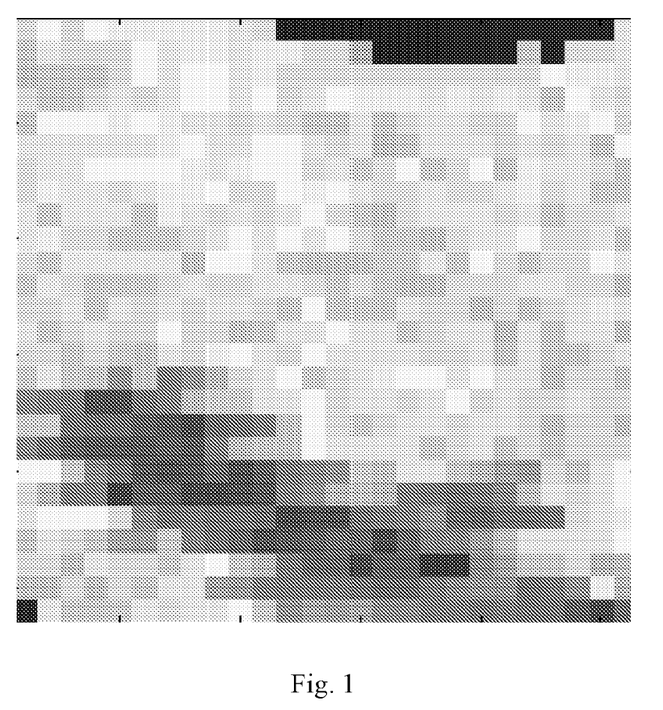
FIG. 1 shows an incoherent background map according to an embodiment of the invention.

FIG. 1 is a visual representation of an incoherent background map of an object. The map shown in FIG. 1 is two dimensional. However it will be appreciated that the map may be one dimensional i.e. the map may indicate the contribution of a plurality of locations arranged along one axis. As can be appreciated from FIG. 1, the map represents a relative contribution of each of the locations to the incoherent radiation. The relative contribution is illustrated in FIG. 1 by the colour or darkness of each location. It will be noted that FIG. 1 is a representation of the map, wherein the map is a data structure, such as an array, which holds data indicative of the relative contribution of each location, as will be explained. Thus the map is not required to be visually displayed, but may only be stored within a memory.

Figure 2:
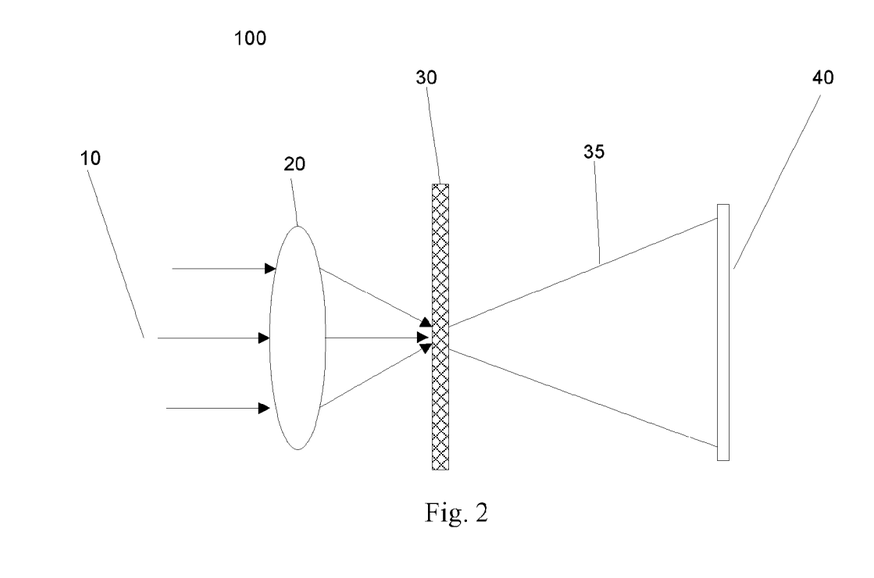
FIG. 2 shows an apparatus according an embodiment of the invention.

FIG. 2 illustrates an apparatus 100 according to an embodiment of the invention. The apparatus is suitable to provide image data of an object which may, although not exclusively, be used to produce an image of at least a region of the object.

A radiation source, which although not shown in FIG. 2, is a source of radiation 10 which falls upon a focusing arrangement 20, such as one or more lenses, and is caused to illuminate a region of a target object 30. It is to be understood that the term radiation is to be broadly construed. The term radiation includes various wave fronts. Radiation includes energy from a radiation source. This will include electromagnetic radiation including X-rays, emitted particles such as electrons. Other types of radiation include acoustic radiation, such as sound waves. Such radiation may be represented by a wave function $\Psi(r)$. This wave function includes a real part and an imaginary part as will be understood by those skilled in the art. This may be represented by the wave functions modulus and phase. $\Psi(r)^*$ is the complex conjugate of $\Psi(r)$ and $\Psi(r)\Psi(r)^* = |\Psi(r)|^2$ where $|\Psi(r)|^2$ is an intensity which may be measured for the wave function.

The lens 20 forms a probe function P(r) which is arranged to select a region of the target object 20 for investigation. The probe function selects part of an object exit wave for analysis. P(r) is the complex stationary value of this wave field calculated at the plane of the object 40.

It will be understood that rather than weakly (or indeed strongly) focusing illumination on the target 40, unfocused radiation can be used with a post target aperture. An aperture is located post target object to thereby select a region of the target for investigation. A pre-target aperture may also be used. The aperture is formed in a mask so that the aperture defines a "support". A support is an area of a function where that function is not zero. In other words outside the support the function is zero. Outside the support the mask blocks the transmittance of radiation. The term aperture describes a localised transmission function of radiation. This may be represented by a complex variable in two dimensions having a modulus value between 0 and 1. An example is a mask having a physical aperture region of varying transmittance.

Incident radiation thus falls upon the up-stream side of the target object 30 and is scattered by the target object 30 as it is transmitted. The target object 30 should be at least partially transparent to incident radiation. The target object 30 may or may not have some repetitive structure. Alternatively the target object 30 may be wholly or partially reflective in which case a scattering pattern is measured based on reflected radiation.

An object function $O(r)$ is thus formed in which $O(r)$ represents a two-dimensional complex function so that each point in $O(r)$, where r is a two-dimensional coordinate, has associated with it a complex number. $O(r)$ will represent a transmission function, such that if $O(r)=1$ for all positions r, the object is entirely transparent, if $O(r)=0$ for all positions r, the object is entirely opaque, but in general $O(r)$ is a complex function having both modulus and phase components. For example, in the case of electron scattering, $O(r)$ would represent the phase and amplitude alteration introduced into an incident plane wave as a result of passing through the object 30 of interest. The probe function $P(r)$ or illumination function selects a part of the object function for analysis. It will be understood that rather than selecting an aperture a transmission grating or other such filtering function may be located downstream of the object function. The probe function $P(r-R)$ is an aperture transmission function where an aperture is at a position R. The probe function can be represented as a complex function with its complex value given by a modulus and phase. The probe function is the complex stationary value of this wave field at the plane of the object. It will also be understood that both the probe and specimen functions may be three-dimensional complex functions, $P(s)$ and $O(s)$, so that each point in $P(s)$ and $O(s)$, where s is a three-dimensional coordinate, has associated with it a complex number.

An exit wave function $\psi(r,R)$ is an exit wave function of radiation as it exits the object 30. This exit wave $\psi(r,R)$ forms a diffraction pattern $\Psi(u)$ at a diffraction plane. Here r is a vector coordinate in real space and u is a vector coordinate in diffraction space.

It will be understood that with both the aperture formed embodiment and the non-aperture embodiment, if the diffraction plane at which scattered radiation is detected is moved nearer to the specimen or object 30 then Fresnel diffraction patterns will be detected rather than Fourier diffraction patterns. In such a case the propagation function from the exit wave $\psi(r,R)$ to the diffraction pattern $\Psi(u)$ will be a Fresnel transform rather than a Fourier transform. It will also be understood that the propagation function from the exit wave $\psi(r,R)$ to the diffraction pattern $\Psi(u)$ may be modelled using other transforms.

In order to select the region of the target object 30 to be illuminated or probed, the lens(es) 20 or aperture may be mounted upon an x/y translation stage which enables movement of the probe function with respect to the object 30. It will also be realised that the object 30 may be moved with respect to the lens(es) or aperture. The probe function 20 may be moved by the translation stage in an arrangement of positions. The arrangement may be a grid. The grid may comprise 20×20 positions, although other numbers of positions may be used and, furthermore, the grid may not comprise equal numbers of positions in both x and y directions. Other arrangements which are envisaged are hexagonal or generally circularly shaped patterns. It will be realised that other shaped arrangements may be used. A random offset may be introduced into a location of each position. For example, if the positions have a pitch of 30 μm, the offset may be in the range ±15 μm. Advantageously, this avoids problems associated with "raster grid pathology".

A detector 40 is a suitable recording device such as a CCD camera or the like which allows the diffraction pattern to be recorded. The detector 40 allows the detection of the diffraction pattern in the diffraction plane. The detector 40 may comprise an array of detector elements, such as in a CCD.

In methods such as those disclosed above, the object and/or radiation source, lens 20 or aperture are moved amongst a plurality of positions. The positions cause the probe function to at least partially overlap that of some of the other probe positions. A diffraction pattern is recorded at each probe position.

It will also be appreciated that embodiments of the invention are envisaged in which a diffraction pattern is simultaneously recorded for each of the plurality of probe positions. Reference is made to co-pending application GB 1207800.2 which is incorporated herein for all purposes. A plurality of diffraction patterns corresponding to a plurality of probe positions may be simultaneously recorded by causing radiation to fall on the target object having a plurality of portions each forming a respective diffraction pattern. A lens may cause each of the portions to be divergent. In other embodiments, an aperture array may be arranged post-target object to simultaneously form a plurality of diffraction patterns. The aperture array may be moved amongst a plurality of positions. Thus references to a plurality of positions may be construed to mean either simultaneously, sequentially or a combination of both.

Figure 3:
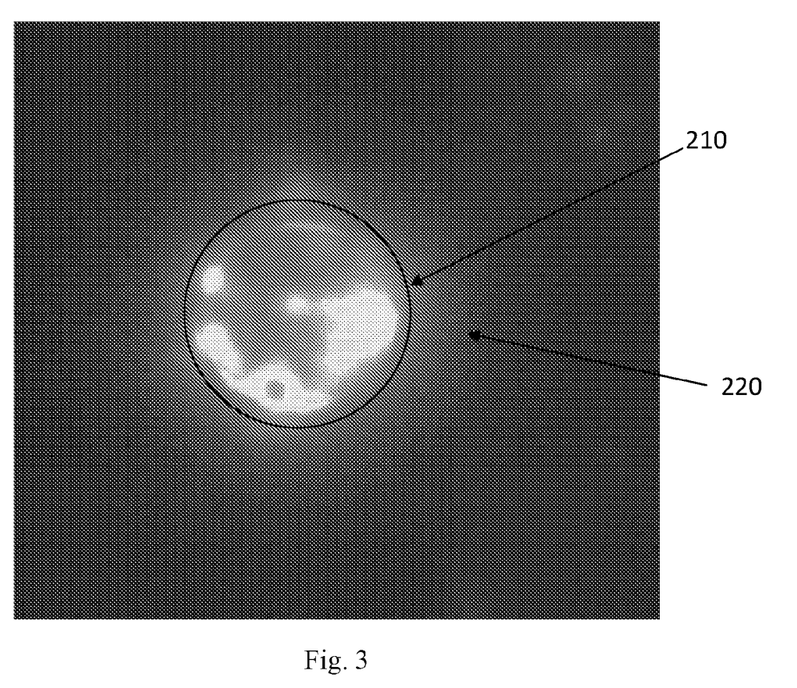
FIG. 3 shows a diffraction pattern recorded by a detector according to an embodiment of the invention.

FIG. 3 illustrates a diffraction pattern recorded by the detector 40 where the radiation 10 is a beam of electrons, although it will be realised that embodiments of the invention are not restricted to this type of radiation. As the incident electrons interact with the object 30, they lose energy which causes their wavelength to change. As can be appreciated from FIG. 3, the recorded diffraction pattern 200 comprises a central brightfield region 210 and a "halo" region 220 extending around a periphery of the brightfield region 210. At least part of the halo 220 results from inelastically scattered electrons which form a background that does not relate directly to the coherent diffraction pattern 210.

In prior art phase retrieval methods, such as the PIE and ePIE methods mentioned above, the contribution due to inelastic scattering recorded by the detector 40 is incoherent with the elastically scattered contribution and may cause the determined probe and/or object function to contain one or more artefacts.

Figure 4:
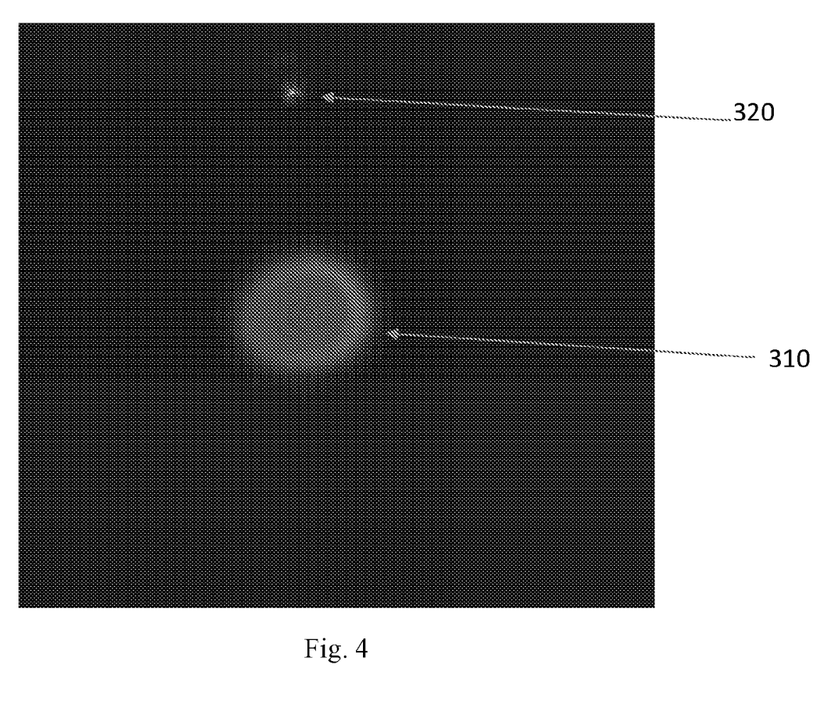
FIG. 4 shows a probe function determined in the presence of an incoherent radiation component.

FIG. 4 illustrates a probe function determined by the ePIE method in the presence of inelastically scattered radiation, as in FIG. 3. The probe function comprises a generally circular component 310 arising from the elastically scattered electron radiation, and an artefact 320 distal from the circular component 310 which is caused by the inelastically scattered radiation. The artefact may form a bright spot 320 outside of an extent of the generally circular component 310 representative of the radiation incident upon the object. Thus it can be appreciated that the reconstructed probe function is not representative of the actual radiation incident upon the object due to the inelastically scattered radiation component.

In order to ameliorate the above-mentioned problem, some embodiments of the invention determine the incoherent background map, such as shown in FIG. 1, which is used to reduce an effect of background radiation measured by the detector, as will be explained.

Figure 5:
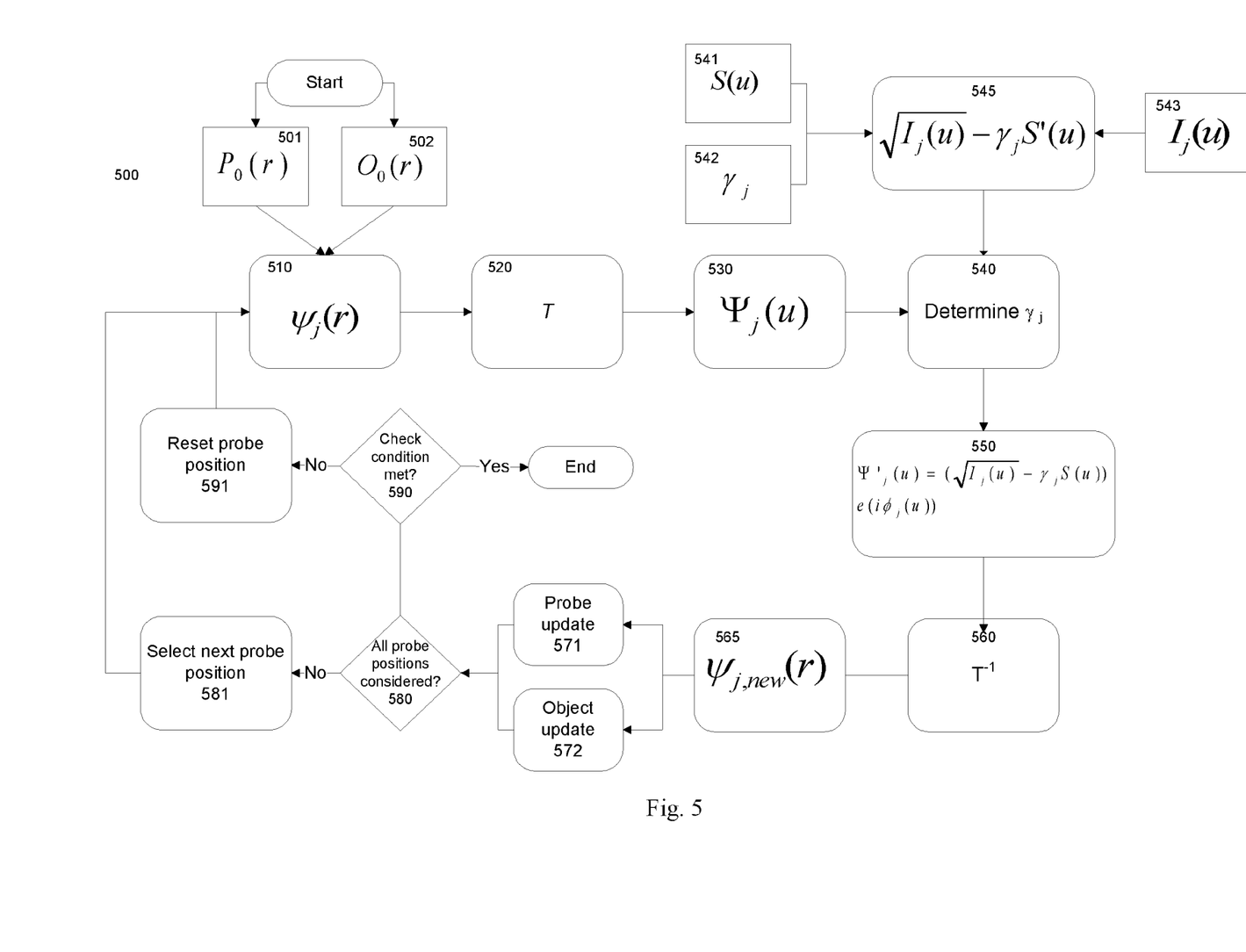
FIG. 5 illustrates a method according to an embodiment of the invention.

FIG. 5 illustrates a method 500 according to an embodiment of the invention. The method 500 illustrated in FIG. 5 involves simultaneous, step-by-step updating of both probe and object function estimates. However, it will be realised that embodiments of the invention may be envisaged in which only the object function is updated and a known probe function is used, as in the methods and apparatus disclosed by WO 2005/106531, for example. Furthermore, in other embodiments of the invention, a known object function may be used and the method may determine the probe function. It will also be appreciated that the object function and/or probe function may be updated by other methods.

The method utilises a set $s(j)$ of $J$ diffracted intensities or diffraction patterns, $I_j(u)$, recorded by the detector 40. Each of the $J$ diffraction patterns may be associated with a different probe position. During each iteration of the method, an estimate of the probe and object function are updated for each of the $J$ diffraction patterns measured by the detector 40. An order of considering each of the $J$ measured intensities is chosen. The order may be numerically sequential i.e. $j=1, 2, 3 \ldots J$. In this case, beginning with diffraction pattern $s(j)$ and progressing through to $s(J)$, updated estimates of the probe $P_1(r) \ldots P_J(r)$ and object $O_1(r) \ldots O_J(r)$ are produced. However, considering the diffraction patterns in a raster fashion (each pattern in a row sequentially and each row sequentially) may cause problems particularly in relation to the estimate of the probe function drifting during the method. Therefore, in some embodiments, the diffraction patterns may be considered in a random or other pseudo-random order. However, for the purposes of explanation, a sequential ordering of the set $s(j)$ will be considered.

At the start of the method 500, prior to a first ($k=1$) iteration, initial probe $P_0(r)$ 501 and object $O_0(r)$ 502 functions are determined; the 0 subscript index indicates that these are initial estimates that will be refined by the method to more closely represent the true functions. The initial probe and object functions 501, 502 may be predetermined initial values, such as initial guesses i.e. pre-calculated approximations, random distributions, or may be based on other initial measurements or prior calculations. The functions 501, 502 are modelled at a number of sample points and are thus represented by matrices. Such matrices can be stored and manipulated by a computer or other such processing unit. Aptly the sample points are equally spaced and form a rectangular array.

In step 510 an estimate of the exit wave $\psi_j(r)$ that produced the $j^{th}$ diffraction pattern is determined by multiplying the current probe 501 and object 502 estimates. For the first ($k=1$) iteration of the method, for the first probe position $s(1)$, the initial object estimate $O_0(r)$ is multiplied by the probe $P_0(r)$ to determine the first exit wave $\psi_1(r)$. For subsequent iterations of the method, the currently selected estimates of the probe and object functions for the jth probe position i.e. $P_j(r)O_j(r)$ are multiplied to determine the current exit wave $\psi_j(r)$.

In step 520 the exit wave $\psi_j(r)$ is propagated to a measurement plane of the detector 40. The propagation produces an estimate 530 $\Psi_j(u)$ of the wavefront at the plane of the detector 40. The exit wave $\psi_j(r)$ is propagated to the measurement plane by a suitable transform T, as shown in equation 1. In some embodiments, the transform T may be a Fourier transform, although in other embodiments the transform may be a Fresnel free space propagator. It is also envisaged that other transforms may be used which are suited to the particular application of the method.

$$\Psi_j(u)=T[\psi_j(r)] \qquad \text{Equation 1}$$

In step 540 a scale factor is determined for the current probe position. The scale factor $\gamma_j$ is used to scale a background function $S(u)$.

The background function $S(u)$ is an estimate of background radiation detected by the detector 40. The background radiation includes a contribution from radiation inelastically scattered by the object 30.

In a first embodiment, the background function $S(u)$ is estimated 541 based upon a determined estimate of the probe function $P_j(r)$. The estimate of the probe function may be determined by the ePIE method noted above. As noted above, in the presence of incoherent background radiation the estimated probe function in the plane of the object after one or more iterations comprises an artefact 320. That is, a phase-retrieval method such as an iterative phase retrieval method for example the ePIE or PIE method may be performed in advance to determine the probe function $P_j(r)$. The estimate of the probe function $P_j(r)$ determined in the presence of inelastically scattered radiation may comprise an artefact such as that shown in FIG. 4.

In the first embodiment, radiation corresponding to the "true" probe function $P_j(r)$ for the probe position is masked out. The masking out may be achieved by setting detected values corresponding to the probe function $P_j(r)$ to a predetermined value, such as 0. In some embodiments this may be achieved by fitting a circular or other shaped mask to the estimate of the elastically scattered radiation (corresponding to the "true" probe function) in the object plane and setting values within the mask to the predetermined value i.e. 0, although other values may be used. The mask may be selected to have a size of greater than the expected "true" probe function. The mask may be selected to have a size of less than a probe window. The probe window is an extent of a data structure storing values for the probe function which may be, for example 512×512 data points although it will be realised that this is merely exemplary.

Values corresponding to the remaining detected radiation including the artefact 320, i.e. outside of the periphery of the probe function, are then used to estimate the background function $S(u)$. The remaining radiation is propagated by a suitable transform, such as a Fourier transform, to the detector plane to provide the estimate of the background function $S(u)$.

In another embodiment, the probe function in the object plane $P_j(r)$ estimated after one or more iterations of the method may be propagated to the detector plane. A free-space diffraction pattern (a diffraction pattern measured without any object in place) may then be subtracted from the estimated probe function to provide an estimate of the background function $S(u)$.

In both embodiments $S(u)$ may be iteratively updated as the algorithm progresses. Either of the above calculations for $S(u)$ may be used as a basis to update $S(u)$. For example the current probe guess may be propagated to the detector plane, then $S(u)$ updated according to the difference between the propagated probe and a free-space diffraction pattern. It will be appreciated that $S(u)$ is updated based upon radiation within the unmasked region i.e. outside of that corresponding to the "true" probe function, whereas the object function is only updated based on radiation corresponding to the "true" probe function.

Figure 6:
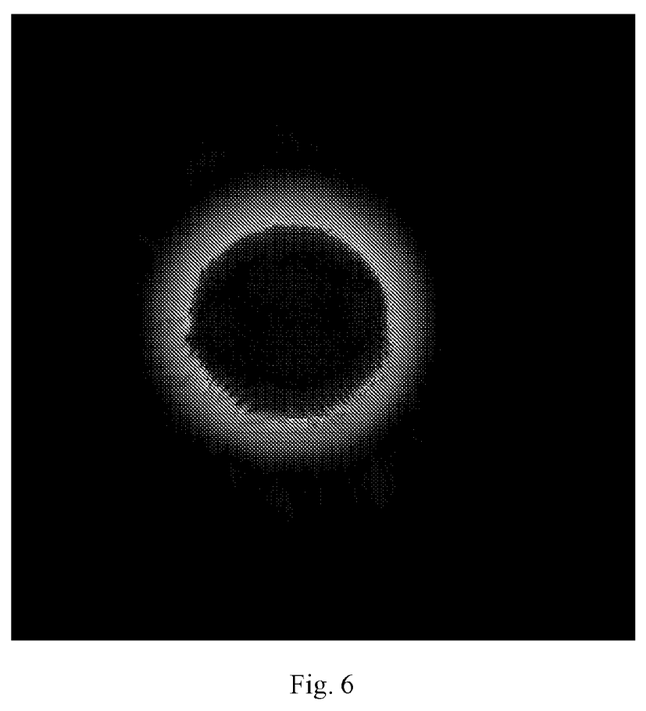
FIG. 6 shows an illustration of a background function according to an embodiment of the invention.

An illustration of the estimated background function at the detector plane is shown in FIG. 6.

The value of the scale factor $\gamma_j$ for the probe position is determined in step 540 to be a value which results in a lowest error between the estimated wavefront (u) and a modulus of the measured diffraction pattern $\sqrt{I_j(u)}$ for the probe position having the background function S(u) subtracted, as in step 545. The scale factor $\gamma_j$ for the probe position may be calculated by least squares fitting, by an iterative process which selects random or pseudo-random values for $\gamma_j$ to obtain a minimum value of $|\sqrt{I_j(u)}-\gamma_j S(u)-\psi_j(u)|$ 545, or another suitable fitting method which may be chosen by the skilled person.

In step 550 at least a portion of the estimated wavefront $\Psi_j$(u) at the plane of the detector 40 is updated based on the measured diffraction pattern $I_j$(u) 545. In some embodiments, the whole i.e. an entire area or extent of the wavefront may be updated, whilst in other embodiments only some of the extent of the wavefront may be updated. As explained in the cited references, since $\Psi_j$(u) is a complex-value, it may be written as shown in equation 2:

$$\Psi_j(u)=A_j(u)\exp(i\phi_j(u)) \quad \text{Equation 2}$$

A modulus of the estimated wavefront may be replaced with Equation 3:

$$\sqrt{I_{s(j)}(u)}-\gamma_j S(u) \quad \text{Equation 3}$$

which is the measured diffraction pattern modulus having the scaled background function subtracted.

In step 560 the revised estimate of the wavefront that produced the $j^{th}$ diffraction pattern $\Psi_j$(u) is reverse propagated back to a plane of the object 30 to provide an updated estimate 565 of the wavefront at the plane of the object 30 $\Psi_{j,new}$(r). The inverse propagation is performed according to the reverse of the transform used in step 520. In some embodiments, the transform used in step 520 is an inverse Fourier transform, although as previously explained other transforms may be used. The inverse transform is performed according to Equation 4:

$$\psi_{j,new}(r)=T^{-1}[\Psi_j(u)] \quad \text{Equation 4}$$

In steps 571 and 572 the probe and object functions are updated. The updating provides an improved probe $P_{j,new}(r)$ and object $O_{j,new}(r)$ function estimate. The updating may be performed as described in the incorporated reference WO 201/064051, or by any other method. Similar to WO 201/064051, the object function may be updated according to Equation 5 and the probe function according to Equation 6:

$$O_{j,new}(r) = O_j(r) + \alpha \frac{P_j^*(r + R_j)}{|P_j(r + R_j)|^2_{max}}(\psi_{j,new}(R) - \psi_j(r)) \quad \text{Equation 5}$$

The parameter α governs the rate of change of the object guess. This value may be adjusted between 0 and 2 as higher values may lead to instability in the updated object guess. According to embodiments of the present invention the probe function is reconstructed in much the same manner as the object function. Aptly the probe function guess is carried out concurrently with the update of the object guess. (It will be appreciated that the probe function could optionally be updated more often or less often than the object function).

$$P_{j,new}(r + R_j) = P_j(r + R) + \beta \frac{O_j^*(r)}{|O_j(r)|^2_{max}}(\psi_{j,new}(r) - \psi_j(r)) \quad \text{Equation 6}$$

The result of this update function generates the running estimate for the probe function. The parameter β governs the rate of change of the probe guess. This value may be adjusted between 0 and 2 as higher values may lead to instability in the updated probe guess.

In step 580 it is determined whether every probe position for the current iteration has been addressed. In other words, it is determined in some embodiments whether j=J. If the current probe position is not the last probe position of the current iteration, then the next probe position is selected. The next probe position may be selected in step 581 by j=j+1. It will also be realised that the next probe position may be randomly selected. However, if the current probe position is the last probe position for the current iteration, then the method moves to step 590.

Once the next probe position has been selected in step 581 or the probe position has been reset in step 591, the method returns to step 510 where an estimate of the wavefront for the probe position is estimated based upon either the initial estimates of the object and probe function for that probe position (for the first iteration of the method for that probe position) or an updated estimate of the object and/or probe function for that probe position.

In step 590 it is determined whether a check condition is met. In some embodiments, the check condition may be determining whether the current iteration number k is a predetermined value, such as k=100 i.e. determining whether a predetermined number of iterations have been performed. Whilst this check is computationally easy, it takes no account of the accuracy of the object and/or probe function estimate(s). Therefore, in some embodiments, the check condition compares a current estimate of the estimated diffraction pattern against that recorded by the detector 40. The comparison may be made considering an error metric such as a sum squared error (SSE) as in equation 7:

$$SSE = \sum_j \frac{\sum_u (|T\psi_j'| - \sqrt{I_j})^2}{\sum_u I_j} \quad \text{Equation 7}$$

The method may end when the error metric meets one or more predetermined criteria, such as being below a predetermined value.

If the predetermined criteria is not met, then the method moves to step 591 in preparation for a next iteration (k=k+1) where the probe position is reset i.e. the first probe position is reselected, such as j=1.

The background map, such as that shown in FIG. 1, is determined by storing the scale factor $\gamma_j$ for each probe position. In some embodiments, the scale factor is stored in a data structure, such as a two dimensional array. Locations having a greater scale factor are shown in FIG. 1 illustrated with a darker colour, thus the respective colours in FIG. 1 indicate a greater magnitude of scale factor $\gamma_j$ for the probe position.

Advantageously, the determination of the scale factor for each probe position allows the estimate of the background radiation to be scaled appropriate for the respective probe position, such that the error introduced by inelastically scatter radiation may be reduced, as will be explained with reference to FIGS. 7 and 8.

Figure 7A:
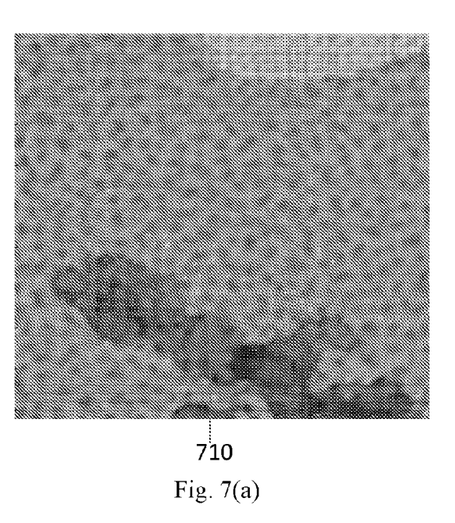
FIG. 7 illustrates an object function determined according to the prior art and according to an embodiment of the invention.
Figure 7B:
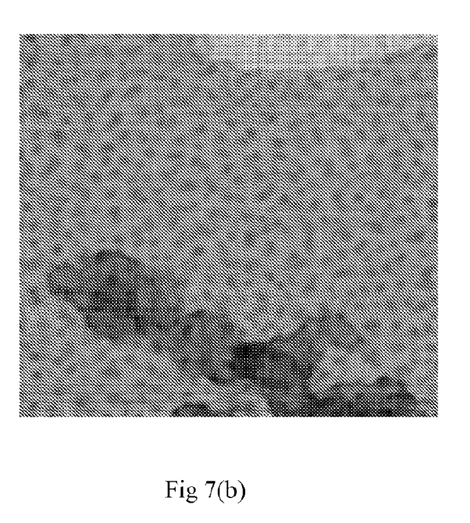

FIG. 7 illustrates the effect of embodiments of the invention. FIG. 7(a) illustrates an object function determined by the prior art ePIE method. As can be appreciated particularly in the ringed area 710, features are present in the determined object function which are not features of the object 30. It can be appreciated from FIG. 7(b) that these features are not present, having been removed by use of the background function scaled according to the background map for each probe position.

Figure 8:
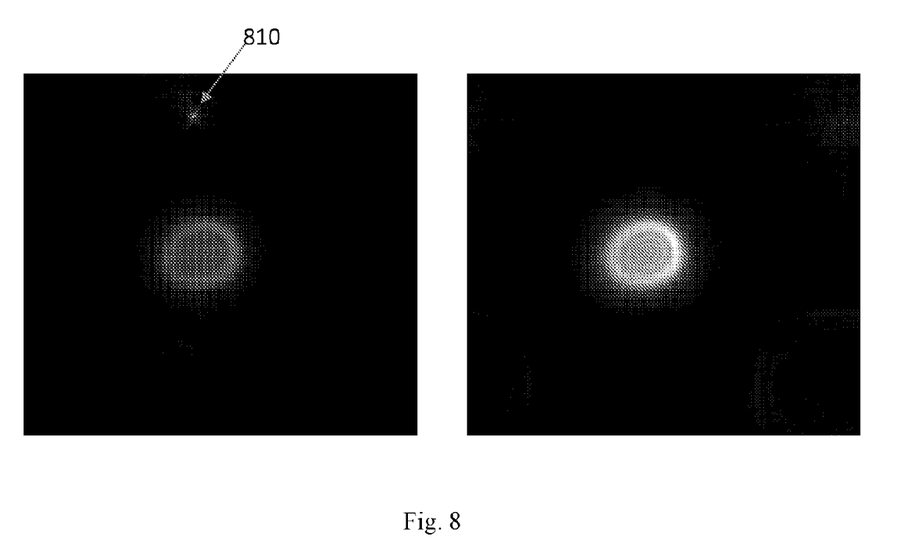
FIG. 8 illustrates a probe function determined according to the prior art and according to an embodiment of the invention.

FIG. 8 further illustrates the effect of embodiments of the invention on a determined probe function. FIG. 8(a) illustrates a probe function determined by the prior art ePIE method. It can be appreciated that an artefact 810 is present in the region beyond the probe function as a result of background inelastically scattered radiation. This artefact is not present in FIG. 8(b) which is produced by an embodiment of the invention.

Figure 9:
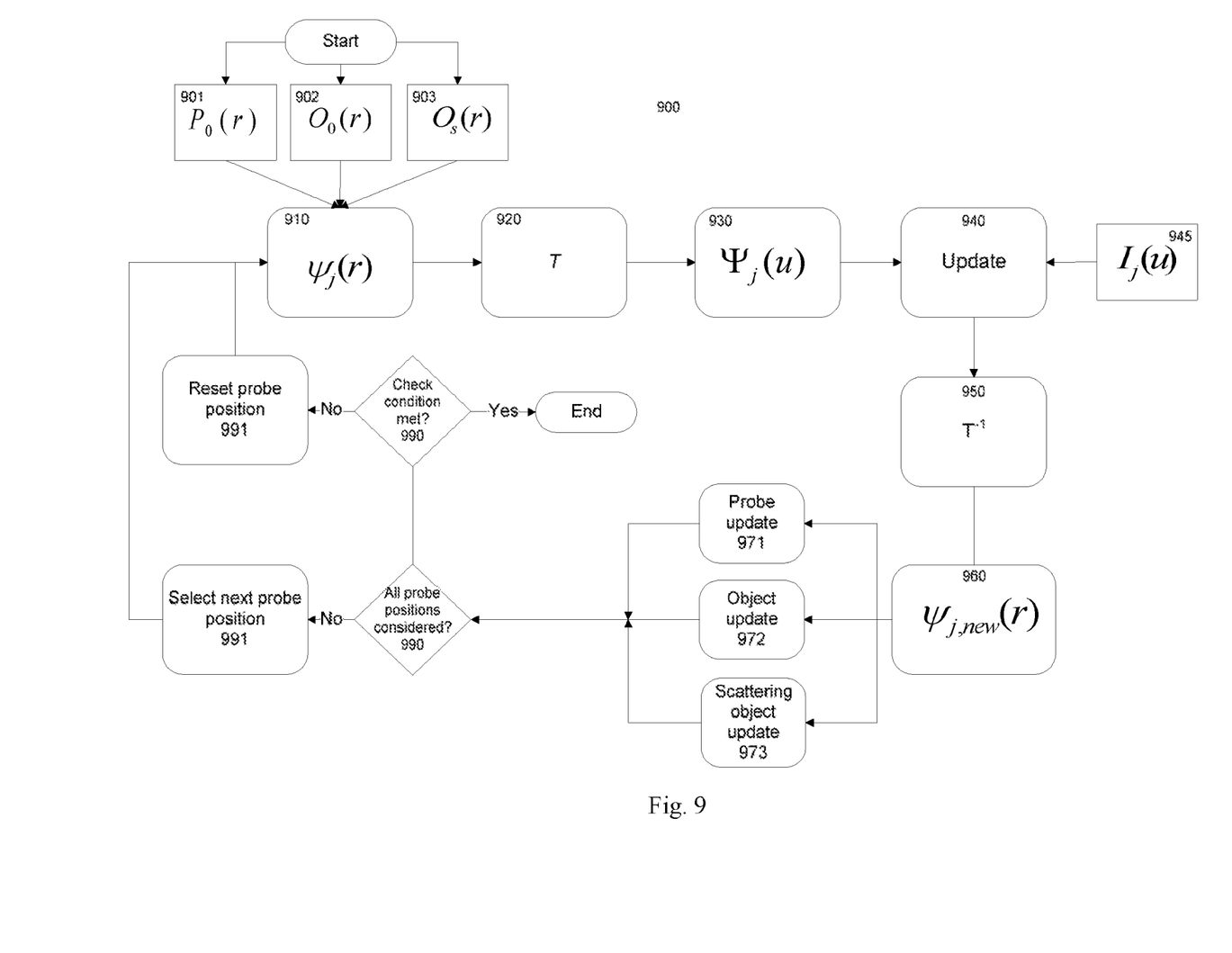
FIG. 9 illustrates a method according to a further embodiment of the invention.

FIG. 9 illustrates a method 900 according to a further embodiment of the invention.

In the method shown in FIG. 9 at least two object function estimates are updated in a step-by-step manner. That is, in an exemplary embodiment, a first object function is determined based upon a probe function within a mask as previously described. The first object function may be determined with respect to radiation corresponding to the "true" probe function, as previously described. One or more further probe functions are determined with respect to radiation not corresponding to the "true" probe function, for example outside of the mask area as will be explained. Whilst an embodiment of the invention is explained with respect to first and second object functions, it will be realised that the invention is not limited in this respect. In particular, the region outside of the "true" probe function may be further divided to into a plurality of areas each having a respective probe function.

Figure 10:
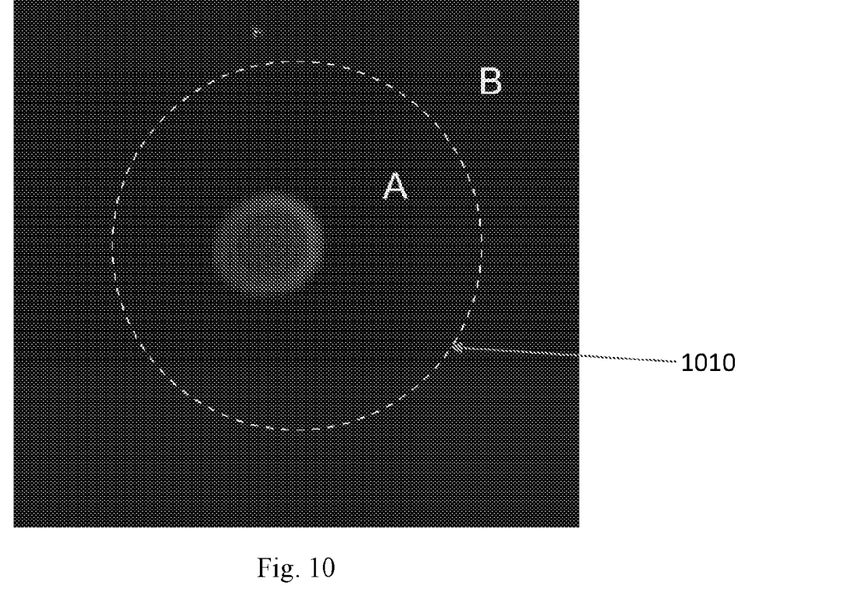
FIG. 10 illustrates a further probe function determined in the presence of an incoherent radiation component.

FIG. 10 illustrates a probe function determined in the presence of incoherent radiation as previously described within a probe window. The probe function may be determined by an iterative method, for example an iterative ptychographic method. The iterative ptychographic method is executed in a prior step to determine the probe function. The probe window is divided into first and second regions identified in FIG. 10 as A and B, wherein region A corresponds to the "true" probe function. The regions A and B are divided by a mask 1010 which is indicated in FIG. 10 with reference 1010. The mask 1010 has a circular shape, although it will be realised that other shaped masks may be used.

In the exemplary embodiment of the invention region A is used as a probe function to determine a first object function corresponding to the object and region B is used to determine a second object function corresponding to incoherent radiation. The first object function is denoted as $O_o(r)$ and the second object function is denoted as $O_s(r)$ wherein the subscript o indicates that the object function is the "true" object function and the subscript s indicates that the object function is a "background" contribution or scattering object function.

As previously described in the incorporated references, an estimate of an exit wave is determined based on a multiplication of estimated object and probe functions. In embodiments of the invention the exit wave is determined based on the probe function, an aperture mask function A and the plurality of object functions. In embodiments of the invention the aperture mask function A can adopt values between first and second values which may be 0 and 1. The aperture mask function effectively, in use, selects between the exit wave contribution from the object and the incoherent radiation, as will be appreciated. The exit wave may be determined as shown in Equation 8:

$$\psi(r)=A \cdot P(r) \cdot O_o(r)+(1-A) \cdot P(r) \cdot O_s(r) \qquad \text{Equation 8}$$

It will be realised that an estimate of the background radiation within the exit wave is included within Equation 8 and may be calculated separately as $sum((1-A)O_s \cdot P)$ where the summation determines the total contribution across all data points. This contribution may be propagated to a plane of the detector, as will be appreciated.

The exit wave $\psi(r)$ is propagated to a plane of the detector using a suitable transform such as a Fourier transform, although it will be realised that embodiments of the invention are not limited in this respect. At a plane of the detector a modulus of the estimated wavefront may be updated as in the prior art using Equation 9:

$$\Psi(u)=\sqrt{I_j(u)} \qquad \text{Equation 9}$$

Even though the exit wave is determined based on a plurality of contributions, it may be updated in this manner due to the linear nature of certain transforms, such as the Fourier transform where $FFT(A+B)=FFT(A)+FFT(B)$. In Equation 8 it will be realised that B is represented as $(1-A)$ where the exit wave comprises two components. However further components may be introduced each term having a respective multiplier e.g. B, C . . . .

Referring again to FIG. 9, at an outset of the method initial guesses or estimates of the probe function $P_0(r)$, object function $O_0(r)$ and scattering object function $O_s(r)$ are provided. In step 910 an exit wave from the object is determined, as explained above for a probe position j, which is then propagated to the plane of the detector in step 920 by a transform T. In step 940 a modulus of the exit wave is updated as explained with reference to Equation 9 and reverse propagated to the plane of the object to provide an updated estimate of the exit wave in step 960. In steps 971, 972, 973 the probe, object and scattering object functions are updated, as explained in the incorporated references.

Therefore it will be appreciated that embodiments of the present invention provide a method and apparatus wherein at least one object function is determined which corresponds to a background radiation component such as due to incoherent radiation.

Figure 11:
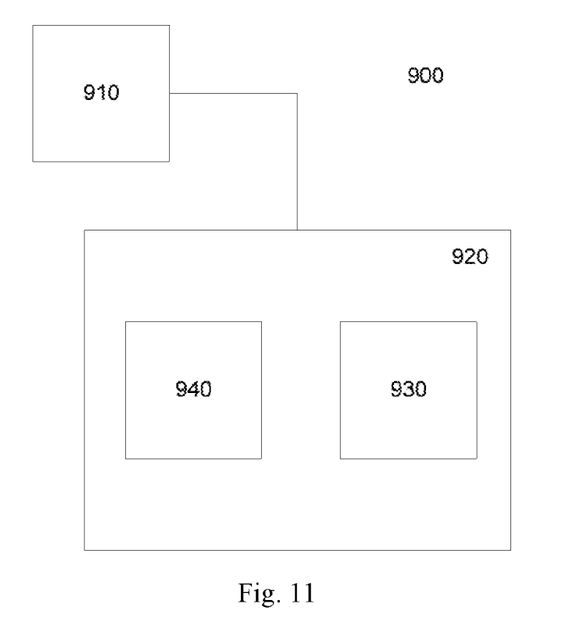
FIG. 11 illustrates an apparatus according to an embodiment of the invention.

FIG. 11 illustrates an apparatus 900 according to an embodiment of the invention. The apparatus 900 is arranged to determine image data for an object. The image data may, in some embodiments, be used to generate a visible image of the object. The visible image may, for example, be output to a display device. In other embodiments the image data may not be used to generate an image, but may be used to determine one or other physical properties of the object, such as physical dimension(s) i.e. thickness, or optical properties of the object.

The apparatus 900 comprises a detector 910 for detecting an intensity of radiation falling thereon. The detector 910 corresponds to the detector 50 shown in FIG. 1 arranged to record a diffraction pattern formed by radiation scattered by the target object. The detector may comprise a plurality of detecting elements each capable of outputting a signal indicative of the intensity of radiation falling thereon. The detector may be a CCD device, or similar. The detector 910 is communicably coupled to a processing unit 920 which is arranged to determine the image data based on the radiation intensity detected by the detector 910. The processing unit 920 comprises a memory 930 and a data processor 940, such as a CPU. Although FIG. 9 shows the processing unit 920 comprising one memory, the processing unit 920 may comprise two or more memories. Furthermore, although shown as comprising one data processor, the processing unit 920 may comprise more than one data processor 940, and each data processor may comprise one or more processing cores. The memory 930 may be arranged to store measured radiation intensity data $I_j(u)$ corresponding to a plurality of probe positions. The data processor 940 may implement a method according to an embodiment of the invention, such as that shown in FIG. 5 or 8 and previously described. The data processor may store determined image data in the memory 930.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of estimating background radiation for each of a plurality of regions of a target object comprising:
   providing an estimate of background radiation detected by a detector;
   measuring radiation scattered by the target object at the detector for each of a plurality of positions of the object with respect to the incident radiation;
   calculating, for each of the positions, an estimate of a wavefront at the detector; and
   determining, for each position, a coherent contribution to the wavefront from radiation scattered by the target object and a background contribution, wherein said background contribution is at least partly incoherent with the radiation scattered by the target object.

2. The method of claim 1, comprising determining, for each position, a scale factor for scaling the estimate of background radiation to reduce a difference between a combination of the estimate of the background radiation and the estimated wavefront, and the measured radiation.

3. The method of claim 1, wherein the estimate of the background radiation is provided by:
   determining an estimate of a probe function for the background radiation at a plane of the object; and
   propagating the estimate of the background radiation to the plane of the detector.

4. The method of claim 3, wherein determining the estimate of the probe function comprises:
   selecting a portion of the estimate of the probe function corresponding to elastically scattered radiation and setting the portion to one or more predetermined values.

5. The method of claim 4, wherein the selecting comprises applying a mask to the estimate of the probe function and setting the portion within the mask to the one or more predetermined values.

6. The method of claim 1, wherein the estimate of the background radiation is provided by:
   propagating an estimate of a probe function at a plane of the object to a plane of the detector; and
   removing a free space diffraction pattern from the estimate at the plane of the detector.

7. The method of claim 2, wherein the scale factor is applied to the estimate of background radiation to reduce a difference between a sum of the estimate of the background radiation and an estimated wavefront, and the measured radiation.

8. The method of claim 2, wherein the scale factor is determined by a fitting process to determine the scale factor having a minimum difference between a combination of the estimate of the background radiation and an estimated wavefront, and the measured radiation.

9. The method of claim 2, wherein the scale factor $\gamma_j$ is determined to find a minimum value of:

$$|\sqrt{I_j(u)} - \gamma_j S(u) - \psi_j(u)|$$

where $I_j(u)$ is an intensity of radiation measured by the detector for the position j, $S(u)$ is the estimate of background radiation detected by the detector, $\psi_j(u)$ is the estimated wavefront.

10. The method of claim 2, comprising storing the scale factor for each of the plurality of positions in a multi-dimensional array.

11. The method of claim 2, wherein at least one of an object function and a probe function are updated based upon the measured radiation and the scaled background radiation to provide an improved estimate of the respective at least one of the object function and the probe function.

12. The method of claim 1, wherein:
   the determining of the coherent contribution of the estimated wavefront comprises determining a first object function; and
   the determining of the background contribution of the estimated wavefront comprises determining a second object function.

13. The method of claim 12, wherein the first object function is determined based on a portion of an estimated probe function corresponding to elastically scattered radiation, and the second object function is determined based on a portion of an estimated probe function corresponding to a further portion of the probe function.

14. The method of claim 12, comprising determining a probe function and dividing the probe function into first and second regions, wherein the first region of the probe function is associated with the first object function and the second region of the probe function is associated with the second object function.

15. The method of any claim 1, wherein the estimate of a wavefront at the detector is determined by a ptychography method.

16. The method of claim 1, wherein the estimate of a wavefront at the detector is determined by multiplying an object function estimate with a probe function estimate to determine an exit wavefront, and propagating the exit wavefront to the plane of the detector.

17. An apparatus, comprising:
a memory storing an estimate of background radiation detected by a detector and data indicative of radiation scattered by a target object for each of a plurality of position of the object with respect to the incident radiation;
a processor arranged to determine, for each position, an estimated wavefront comprising a coherent contribution from radiation scattered by the target object and a background contribution, wherein said background contribution is at least partly incoherent with the radiation scattered by the target object.

18. The apparatus of claim 17, wherein the processor is arranged to determine a scale factor for scaling the estimate of background radiation to reduce a difference between a combination of the estimate of the background radiation and the estimate of the wavefront, and the measured radiation.

19. The apparatus of claim 18, wherein the scale factor is applied to the estimate of background radiation to reduce a difference between a sum of the estimate of the background radiation and an estimated wavefront, and the measured radiation.

20. The apparatus of claim 18, wherein the processor is arranged to perform a fitting process to determine the scale factor resulting in a minimum difference between a combination of the estimate of the background radiation and an estimated wavefront, and the measured radiation.

21. The apparatus of claim 18, wherein the scale factor $\gamma_j$ is determined to find a minimum value of:

$$|\sqrt{I_j(u)} - \gamma_j S(u) - \psi_j(u)|$$

where $I_j(u)$ is an intensity of radiation measured by the detector for the position j, $S(u)$ is the estimate of background radiation detected by the detector, $\psi_j(u)$ is the estimated wavefront.

22. The apparatus of claim 18, comprising storing the scale factor for each of the plurality of positions in a multi-dimensional array in the memory.

23. The apparatus of claim 18, wherein:
the determining of the coherent contribution of the estimated wavefront comprises the processor determining a first object function; and
the determining of the background contribution of the estimated wavefront comprises the processor determining a second object function.

24. The apparatus of claim 23, wherein the first object function is determined based on a portion of a portion of an estimated probe function corresponding to elastically scattered radiation, and the second object function is determined based on a portion of an estimated probe function corresponding to a further portion of the probe function.

25. The apparatus of claim 23, wherein the processor is arranged to determine a probe function and divide the probe function into at least first and second regions, wherein the first region of the probe function is associated with the first object function and the second region of the probe function is associated with the second object function.

26. The apparatus of claim 17, wherein the coherent contribution and the incoherent contribution are separately determined.

27. The apparatus of claim 17, comprising the detector for measuring an intensity of radiation scattered by the target object.

28. The method of claim 1, wherein the background radiation is substantially inelastically scattered radiation.

29. Computer software tangibly stored on a computer readable medium which, when executed by a computer, is arranged to perform the method of claim 1.

* * * * *